US 12,256,945 B2

(12) United States Patent
Vu et al.

(10) Patent No.: US 12,256,945 B2
(45) Date of Patent: *Mar. 25, 2025

(54) SURGICAL BURS

(71) Applicant: Medtronic PS Medical, Inc., Fort Worth, TX (US)

(72) Inventors: Michael Vu, Grand Prairie, TX (US); Donald E. Stearns, Fort Worth, TX (US)

(73) Assignee: Medtronic PS Medical, Inc., Goleta, CA (US)

( * ) Notice: Subject to any disclaimer, the term of this patent is extended or adjusted under 35 U.S.C. 154(b) by 204 days.

This patent is subject to a terminal disclaimer.

(21) Appl. No.: 17/881,050

(22) Filed: Aug. 4, 2022

(65) Prior Publication Data

US 2022/0378439 A1    Dec. 1, 2022

Related U.S. Application Data

(60) Continuation of application No. 16/390,476, filed on Apr. 22, 2019, now Pat. No. 11,406,396, which is a division of application No. 14/840,217, filed on Aug. 31, 2015, now Pat. No. 10,265,082.

(51) Int. Cl.
*A61B 17/16* (2006.01)

(52) U.S. Cl.
CPC .......... *A61B 17/16* (2013.01); *A61B 17/1615* (2013.01); *A61B 17/1695* (2013.01); *A61B 17/1628* (2013.01)

(58) Field of Classification Search
CPC . A61B 17/16; A61B 17/1613; A61B 17/1615; A61B 17/1617; A61B 17/1622; A61B 17/1628; A61B 17/1695
See application file for complete search history.

(56) References Cited

U.S. PATENT DOCUMENTS

| | | | |
|---|---|---|---|
| 180,554 | A | 8/1876 | Cubberley |
| 372,400 | A | 11/1887 | Browne |
| 533,573 | A | 2/1895 | Wilkens |
| 533,673 | A | 2/1895 | Wilkens |
| 662,349 | A | 11/1900 | Burton |
| 1,309,706 | A | 7/1919 | Taylor |
| 2,795,979 | A | 6/1957 | Zerwick |
| 2,847,885 | A | 8/1958 | Wagner |
| 2,847,895 | A | 8/1958 | Wagner |

(Continued)

FOREIGN PATENT DOCUMENTS

| | | |
|---|---|---|
| CN | 101743085 A | 6/2010 |
| CN | 101745679 A | 6/2010 |

(Continued)

OTHER PUBLICATIONS

Korean 1st Office Action corresponding to PCT/US2016/049464, Mailing Date: Jul. 6, 2023.

(Continued)

*Primary Examiner* — Eric S Gibson
(74) *Attorney, Agent, or Firm* — Carter, DeLuca & Farrell LLP (57) ABSTRACT

A surgical bur is disclosed having cutting and trailing edges and associated flutes and lands. Each flute includes a cutting edge. Each of the trailing edges relatives in a selected dimension to a preceding cutting edge.

20 Claims, 4 Drawing Sheets

(56) References Cited

U.S. PATENT DOCUMENTS

| | | |
|---|---|---|
| 2,878,701 A | 3/1959 | Weersma |
| 2,903,922 A | 9/1959 | Ernst |
| 3,387,511 A | 6/1968 | Ackart, Sr. |
| 3,387,554 A | 6/1968 | Cherre |
| 3,872,594 A | 3/1975 | Gerteisen |
| 3,937,222 A | 2/1976 | Banko |
| 4,441,563 A | 4/1984 | Walton, II |
| 4,445,509 A | 5/1984 | Auth |
| 4,594,034 A | 6/1986 | Maier |
| 4,600,006 A | 7/1986 | Baker |
| 4,602,900 A | 7/1986 | Arpaio, Jr. et al. |
| 4,699,550 A | 10/1987 | Baker |
| 4,740,121 A | 4/1988 | Arnold |
| 4,803,982 A | 2/1989 | Baker |
| 4,830,000 A | 5/1989 | Shutt |
| 4,951,690 A | 8/1990 | Baker |
| 4,975,003 A | 12/1990 | Hosoi |
| 4,978,350 A | 12/1990 | Wagenknecht |
| 5,007,911 A | 4/1991 | Baker |
| 5,011,342 A | 4/1991 | Hsu |
| 5,013,194 A | 5/1991 | Wienhold |
| 5,122,134 A | 6/1992 | Borzone et al. |
| 5,143,490 A | 9/1992 | Kopras |
| 5,190,548 A | 3/1993 | Davis |
| 5,209,612 A | 5/1993 | Kish |
| 5,236,291 A | 8/1993 | Agapiou et al. |
| 5,302,059 A | 4/1994 | Fabiano |
| 5,336,673 A | 8/1994 | Moon et al. |
| 5,429,504 A | 7/1995 | Peltier et al. |
| 5,467,837 A | 11/1995 | Miller et al. |
| 5,514,141 A | 5/1996 | Prizzi, Jr. |
| 5,575,650 A | 11/1996 | Niznick et al. |
| 5,579,185 A | 11/1996 | Tsai et al. |
| D378,780 S | 4/1997 | Shuler |
| 5,618,293 A | 4/1997 | Sample et al. |
| 5,634,933 A | 6/1997 | McCombs et al. |
| 5,658,305 A | 8/1997 | Baker |
| 5,741,263 A | 4/1998 | Umber et al. |
| 5,759,185 A | 6/1998 | Grinberg |
| 5,794,715 A | 8/1998 | Norman |
| 5,810,517 A | 9/1998 | Bostic |
| 5,833,402 A | 11/1998 | Martin |
| 5,846,035 A | 12/1998 | Karafillis et al. |
| 5,855,581 A | 1/1999 | Koblish et al. |
| 5,860,773 A | 1/1999 | Blomberg et al. |
| 5,888,200 A | 3/1999 | Walen |
| 5,893,851 A | 4/1999 | Umber et al. |
| 5,913,867 A | 6/1999 | Dion |
| 5,928,241 A | 7/1999 | Menut et al. |
| 5,934,846 A | 8/1999 | Ishii |
| 5,964,553 A | 10/1999 | Blomberg et al. |
| 5,980,525 A | 11/1999 | Bryant et al. |
| 6,045,564 A | 4/2000 | Walen |
| 6,068,632 A | 5/2000 | Carchidi et al. |
| 6,132,448 A | 10/2000 | Perez et al. |
| 6,238,398 B1 | 5/2001 | Lechot |
| 6,258,093 B1 | 7/2001 | Edwards et al. |
| 6,332,886 B1 | 12/2001 | Green et al. |
| 6,431,801 B2 | 8/2002 | Vasudeva et al. |
| 6,435,780 B1 | 8/2002 | Flynn |
| 6,511,493 B1 | 1/2003 | Moutafis et al. |
| 6,514,258 B1 | 2/2003 | Brown et al. |
| 6,547,495 B2 | 4/2003 | Meece et al. |
| 6,562,046 B2 | 5/2003 | Sasso |
| 6,562,055 B2 | 5/2003 | Walen |
| 6,579,298 B1 | 6/2003 | Bruneau et al. |
| 6,682,349 B1 | 1/2004 | Logeart |
| 6,780,189 B2 | 8/2004 | Tidwell et al. |
| 6,783,533 B2 | 8/2004 | Green et al. |
| 7,001,391 B2 | 2/2006 | Estes et al. |
| 7,011,661 B2 | 3/2006 | Riedel et al. |
| 7,066,940 B2 | 6/2006 | Riedel et al. |
| 7,520,703 B2 | 4/2009 | Rompel |
| 7,549,992 B2 | 6/2009 | Shores et al. |
| 7,559,927 B2 | 7/2009 | Shores et al. |
| 7,669,860 B2 | 3/2010 | Chiang |
| 7,845,428 B2 | 12/2010 | Sakamaki et al. |
| 7,862,263 B2 | 1/2011 | van Iperen |
| 8,016,830 B2 | 9/2011 | Veldman et al. |
| 8,132,990 B2 | 3/2012 | Bauman |
| 8,414,228 B2 | 4/2013 | Wells et al. |
| 8,460,298 B2 | 6/2013 | O'Donoghue |
| 8,465,492 B2 | 6/2013 | Estes |
| 8,529,567 B2 | 9/2013 | Garcia et al. |
| 8,607,673 B2 | 12/2013 | Marson |
| 8,852,222 B2 | 10/2014 | O'Sullivan |
| 8,882,113 B2 | 11/2014 | Porter et al. |
| 9,179,923 B2* | 11/2015 | Gubellini ............ A61B 17/1615 |
| 9,186,156 B2 | 11/2015 | Xie |
| 9,232,952 B2 | 1/2016 | Kulas et al. |
| 9,414,848 B2 | 8/2016 | Edwards et al. |
| 9,504,478 B2 | 11/2016 | Edwards et al. |
| 9,526,508 B2 | 12/2016 | Burke et al. |
| 9,566,121 B2 | 2/2017 | Staunton et al. |
| 9,585,676 B1 | 3/2017 | Russo et al. |
| 9,883,873 B2 | 2/2018 | Kulas et al. |
| 9,924,952 B2 | 3/2018 | Kulas et al. |
| 9,936,975 B2 | 4/2018 | Siemer et al. |
| 9,955,981 B2* | 5/2018 | Kulas ................. A61B 17/1617 |
| 10,265,082 B2* | 4/2019 | Vu ..................... A61B 17/1695 |
| 10,265,084 B2 | 4/2019 | Ujvari |
| 10,335,166 B2* | 7/2019 | Kulas ................. A61B 17/1695 |
| 10,507,028 B2* | 12/2019 | Kulas ................. A61B 17/1615 |
| 10,786,266 B2* | 9/2020 | Kulas ................. A61B 17/1695 |
| 11,076,871 B2 | 8/2021 | Barnes |
| 11,406,396 B2* | 8/2022 | Vu ..................... A61B 17/1695 |
| 2003/0097133 A1 | 5/2003 | Green et al. |
| 2004/0057803 A1 | 3/2004 | Walrath |
| 2004/0081523 A1 | 4/2004 | Vasudeva et al. |
| 2004/0122460 A1 | 6/2004 | Shores et al. |
| 2004/0155414 A1 | 8/2004 | Baldwin et al. |
| 2004/0232631 A1 | 11/2004 | Chen et al. |
| 2005/0053439 A1 | 3/2005 | Wang et al. |
| 2005/0203526 A1 | 9/2005 | Ellis |
| 2005/0272004 A1 | 12/2005 | Desrosiers |
| 2005/0273107 A1 | 12/2005 | Stevens |
| 2005/0283160 A1 | 12/2005 | Knisely et al. |
| 2006/0045639 A1 | 3/2006 | Flynn et al. |
| 2006/0067797 A1 | 3/2006 | Calamia |
| 2006/0085005 A1 | 4/2006 | Kenealy et al. |
| 2006/0129061 A1 | 6/2006 | Kaneto et al. |
| 2006/0142775 A1 | 6/2006 | Heneberry et al. |
| 2006/0269372 A1 | 11/2006 | Goshima |
| 2007/0010822 A1 | 1/2007 | Zalenski et al. |
| 2007/0160437 A1* | 7/2007 | Shultz .................... B23B 51/02 |
| | | 408/230 |
| 2007/0163416 A1 | 7/2007 | Burgess |
| 2007/0213736 A1 | 9/2007 | Ducharme |
| 2007/0280792 A1 | 12/2007 | Kochan et al. |
| 2007/0298376 A1 | 12/2007 | Kmiecz et al. |
| 2008/0132929 A1 | 6/2008 | O'Sullivan et al. |
| 2008/0140078 A1 | 6/2008 | Nelson et al. |
| 2008/0167653 A1 | 7/2008 | Watlington et al. |
| 2008/0177294 A1 | 7/2008 | O'Neil et al. |
| 2008/0193234 A1 | 8/2008 | Davancens et al. |
| 2008/0215148 A1 | 9/2008 | Lesinski et al. |
| 2008/0246233 A1 | 10/2008 | Wienhold |
| 2009/0023988 A1 | 1/2009 | Korner et al. |
| 2009/0024129 A1 | 1/2009 | Gordon et al. |
| 2009/0048602 A1 | 2/2009 | O'Donoghue |
| 2009/0138015 A1 | 5/2009 | Conner et al. |
| 2009/0216235 A1 | 8/2009 | Ellis |
| 2009/0222009 A1 | 9/2009 | Ellis |
| 2009/0264888 A1 | 10/2009 | Neumeyer et al. |
| 2010/0054884 A1 | 3/2010 | Masuda et al. |
| 2010/0057087 A1 | 3/2010 | Cha |
| 2010/0121365 A1 | 5/2010 | O'Sullivan et al. |
| 2010/0145341 A1 | 6/2010 | Ranck et al. |
| 2010/0178631 A1 | 7/2010 | Gordils Wallis et al. |
| 2010/0209200 A1 | 8/2010 | Delacretaz |
| 2010/0286695 A1 | 11/2010 | Hannani et al. |
| 2011/0015634 A1 | 1/2011 | Smith et al. |
| 2011/0054884 A1 | 3/2011 | Drakwall et al. |
| 2011/0098710 A1 | 4/2011 | Spratt et al. |

(56) References Cited

U.S. PATENT DOCUMENTS

| | | |
|---|---|---|
| 2011/0112540 A1 | 5/2011 | McLean et al. |
| 2011/0196380 A1 | 8/2011 | Cremer et al. |
| 2011/0208194 A1 | 8/2011 | Steiner et al. |
| 2011/0211922 A1 | 9/2011 | Maeda et al. |
| 2011/0238070 A1 | 9/2011 | Santangelo et al. |
| 2011/0238099 A1 | 9/2011 | Loreth |
| 2011/0260415 A1 | 10/2011 | Lin |
| 2011/0301578 A1 | 12/2011 | Muniz-Medina et al. |
| 2012/0063860 A1 | 3/2012 | Wada et al. |
| 2012/0150209 A1* | 6/2012 | Gubellini ............ A61B 17/1615 606/170 |
| 2012/0158028 A1 | 6/2012 | O'Sullivan et al. |
| 2012/0259337 A1 | 10/2012 | del Rio et al. |
| 2012/0283706 A1 | 11/2012 | Blust |
| 2012/0330315 A1 | 12/2012 | Ranck et al. |
| 2013/0028677 A1 | 1/2013 | Schwaegert et al. |
| 2013/0051937 A1 | 2/2013 | Volokh et al. |
| 2013/0166034 A1 | 6/2013 | Landon |
| 2013/0245704 A1 | 9/2013 | Koltz et al. |
| 2013/0274779 A1* | 10/2013 | Kulas ................. A61B 17/1615 606/180 |
| 2014/0058423 A1 | 2/2014 | Smith et al. |
| 2015/0025559 A1* | 1/2015 | Kulas ................. A61B 17/1615 606/180 |
| 2015/0037111 A1 | 2/2015 | Chang |
| 2015/0173776 A1 | 6/2015 | Burke et al. |
| 2015/0297243 A1* | 10/2015 | Kulas ................. A61B 17/1695 606/80 |
| 2015/0327905 A1 | 11/2015 | Barth et al. |
| 2016/0031017 A1 | 2/2016 | Peters et al. |
| 2016/0287267 A1 | 10/2016 | Kulas et al. |
| 2017/0056026 A1* | 3/2017 | Vu ........................ A61B 17/16 |
| 2017/0282257 A1 | 10/2017 | Wang |
| 2018/0055519 A1 | 3/2018 | Barnes |
| 2018/0153562 A1* | 6/2018 | Kulas ................. A61B 17/1615 |
| 2018/0206855 A1* | 7/2018 | Kulas ................. A61B 17/1615 |
| 2018/0242986 A1* | 8/2018 | Kulas ................. A61B 17/1615 |
| 2019/0239898 A1* | 8/2019 | Vu ..................... A61B 17/1615 |
| 2022/0378439 A1* | 12/2022 | Vu ..................... A61B 17/1695 |

FOREIGN PATENT DOCUMENTS

| | | |
|---|---|---|
| CN | 201565651 U | 9/2010 |
| CN | 103079756 A | 5/2013 |
| CN | 204562293 U | 8/2015 |
| DE | 9214609 U1 | 12/1992 |
| DE | 19826276 C1 | 11/1999 |
| DE | 102010010589 A1 | 9/2011 |
| EP | 0332437 A3 | 8/1990 |
| EP | 1872739 A1 | 1/2008 |
| EP | 2561822 A2 | 2/2013 |
| EP | 3698731 A1 | 8/2020 |
| GB | 2452158 A | 2/2009 |
| JP | S59-127476 A | 7/1984 |
| JP | S59-150263 A | 8/1984 |
| JP | H06155126 A | 6/1994 |
| JP | H07108409 A | 4/1995 |
| JP | H10-263914 A | 10/1998 |
| JP | 2003291024 A | 10/2003 |
| JP | 2005125465 A | 5/2005 |
| JP | 2006512214 A | 4/2006 |
| JP | 2006523542 A | 10/2006 |
| JP | 2008501541 A | 1/2008 |
| JP | 200923055 A | 2/2009 |
| JP | 2010-510042 A | 4/2010 |
| JP | 2013502943 A | 1/2013 |
| JP | 2013527781 A | 7/2013 |
| JP | 2013166232 A | 8/2013 |
| JP | 2014-121194 A | 6/2014 |
| KR | 10-2012-0067346 A | 6/2012 |
| WO | 2006/026482 A2 | 3/2006 |
| WO | 2007010389 A1 | 1/2007 |
| WO | 2008061711 A2 | 5/2008 |
| WO | 2008064350 A2 | 5/2008 |
| WO | 2009063261 A1 | 5/2009 |
| WO | 2010061933 A1 | 6/2010 |
| WO | 2011023381 A1 | 3/2011 |
| WO | 2011132876 A2 | 10/2011 |
| WO | 2012083468 A1 | 6/2012 |
| WO | 2013056262 A1 | 4/2013 |
| WO | 2013/151770 A1 | 10/2013 |
| WO | 2013158469 A1 | 10/2013 |
| WO | 2014037518 A1 | 3/2014 |
| WO | 2015009810 A1 | 1/2015 |
| WO | 2015160884 A1 | 10/2015 |

OTHER PUBLICATIONS

Office Action mailed Mar. 1, 2019 in corresponding Canadian Application No. 2,945,806.

Australian Office Action dated Jun. 23, 2015 for AU Application No. 2013249626 for PCT/US2013/036269 which claims benefit of U.S. Appl. No. 13/447,372, filed Apr. 16, 2012.

Canadian Office Action dated Sep. 29, 2015 for Canadian Application No. 2,870,689 claiming benefit of PCT/US2013/036269.

Canadian Office Action dated Aug. 4, 2016 for CA Application No. 2870689 for PCT/US2013/036269 which claims benefit of U.S. Appl. No. 13/447,372, filed Apr. 16, 2012.

Canadian Office Action mailed Sep. 29, 2015 for Canadian Application 2,870,689 claiming benefit of International Application PCT/US2013/036269 claiming benefit of U.S. Appl. No. 13/447,372, filed Apr. 16, 2012.

Chinese Office Action (English translation) dated May 24, 2016 for Chinese Application No. 2013800311659 which claims benefit of PCT/2013/036269 filed Apr. 12, 2013.

End Mill and Cutting Tool Design Criteria and Technical Features. Melin Tool Company. Retrieved from <http://www.endmill.com/pages/training/design.html on Jun. 14, 2013. (pp. 1-4).

European Office Action dated Dec. 15, 2015 for EP Application No. 13720176.0-1654.

European Office Action dated Dec. 15, 2015 for European Application No. 13720176.0-1654 claiming benefit of PCT/US2013/036269.

Find Your Perfect Balance. Midas Rex Legend 7.5. cm Attachments and Tools. Medtronic brochure. (2012) 3 pages.

Innovations 2005 catalog, Komet Gebr. Brasseler GmbH & Co., KG, Lemgo, Germany, 28 pages.

International Preliminary Report on Patentability and Written Opinion mailed Jan. 19, 2016 for PCT/US2014/046827, claiming priority to U.S. Appl. No. 13/944,650, filed Jul. 17, 2013.

International Preliminary Report on Patentability and Written Opinion mailed Jan. 28, 2016 for PCT/US2014/046827 which claims benefit of U.S. Appl. No. 13/944,650, filed Jul. 17, 2013.

International Preliminary Report on Patentability and Written Opinion mailed Oct. 30, 2014 for PCT/US2013/036269, claiming priority to U.S. Appl. No. 13/447,372, filed Apr. 16, 2012.

International Preliminary Report on Patentability dated Oct. 27, 2016 for Application No. PCT/US2015/025867 filed Apr. 15, 2015.

International Search Report and Written Opinion dated Jan. 3, 2017 for PCT/US2016/049464 claiming benefit of U.S. Appl. No. 14/840,217, filed Aug. 31, 2015.

International Search Report and Written Opinion dated Jul. 25, 2016 for PCT/US2016/023349 which claims benefit the benefit of U.S. Appl. No. 14/674,002, filed Mar. 31, 2015.

International Search Report and Written Opinion mailed Aug. 28, 2013 for PCT/US2013/036269, claiming priority to U.S. Appl. No. 13/447,372, filed Apr. 16, 2012.

International Search Report and Written Opinion mailed Jan. 19, 2016 for Application No. PCT/US2014/046827 which claims benefit of U.S. Appl. No. 13/944,650, filed Jul. 17, 2013.

International Search Report and Written Opinion mailed Jul. 25, 2016 for Application No. PCT/US2014/046827 which claims benefit of U.S. Appl. No. 13/944,650, filed Jul. 17, 2013.

International Search Report and Written Opinion mailed Oct. 10, 2014 for PCT/US2014/046827 claiming benefit of U.S. Appl. No. 13/944,650, filed Jul. 17, 2013.

(56) References Cited

OTHER PUBLICATIONS

International Search Report and Written Opinion mailed Oct. 22, 2015 corresponding to PCT/US2015/025867 filed Apr. 15, 2015.
Japanese Office Action mailed Nov. 10, 2015 for Japanese Application No. 2015-507064 claiming benefit of PCT/US2014/046827 claiming benefit of U.S. Appl. No. 13/944,650, filed Jul. 17, 2013.
Japanese Office Action mailed Nov. 10, 2015 for Japanese Application 2015-507064 claiming benefit of PCT/US2014/046827 claiming benefit of U.S. Appl. No. 13/944,650, filed Jul. 17, 2013.
Japanese Office Action mailed Jun. 21, 2016 for Japanese Application No. 2015-50764 claiming benefit of PCT/US2013/036269 claiming benefit of U.S. Appl. No. 13/447,372, filed Apr. 12, 2013 with English translation.
Komet Burs mini catalogue 2007, Henry Schein Halas, www.henryschein.com.au, 19 pages.
Komet Surgery catalog, Mar. 2011, 8 pages.
Korean Office Action dated Mar. 16, 2016 for KR Application No. 10-2014-7031869 for PCT/US2013/036269 which claims benefit of U.S. Appl. No. 13/447,372, filed Apr. 16, 2012 with English translation.
Korean Office Action mailed Sep. 30, 2016 for Korean Application No. 10-2014-7031869 corresponding to PCT/US2013/036269 which claims benefit of U.S. Appl. No. 13/447,372, filed Apr. 16, 2012 with English translation.
Stryker Neuro Spine ENT brochure, Zyphr Burs, Kalamazoo, Michigan, www.stryker.com, 2011, 6 pages.
Table of Contents, RedLine Tools catalog, www.redlinetools.com/Images/PDFs/Redline09/RL062009_Sec1_Front%20pl-9_72.pdf, pp. 1-8.
Australian Office Action mailed Mar. 15, 2017 for AU Application No. 2015247768.
Canadian Office Action mailed May 1, 2017 for CA Application No. 2,917,601.
Extended European Search Report mailed Jul. 3, 2017 in corresponding European Application No. 17151461.5.
European Office Action mailed Jul. 27, 2017 in corresponding European Application No. 14747254.2.
International Preliminary Report on Patentability mailed Oct. 12, 2017 in corresponding International Application No. PCT/US2016/023349.
Canadian Office Action mailed Aug. 22, 2017 in corresponding/related Canadian Application No. 2,945,806.
Canadian Office Action mailed Feb. 2, 2018 in corresponding/related Canadian Application No. 2,917,601.
Korean Office Action mailed Feb. 19, 2018 in corresponding/related Korean Application No. 10-2016-7031697.
Australian Office Action mailed Mar. 21, 2018 in corresponding/related Australian Application No. 2016234968.
International Preliminary Report on Patentability mailed Mar. 15, 2018 in corresponding/related International Application No. PCT/US2016/049464.
Japanese Office Action mailed Apr. 19, 2018 in corresponding/related Japanese Application No. 2016-527065.
Australian Office Action mailed Apr. 12, 2018 in corresponding/related Australian Application No. 2014290106.
Canadian Office Action mailed Jun. 7, 2018 in corresponding/related Canadian Application No. 2,945,806.
Korean Office Action mailed Jul. 12, 2018 in corresponding/related Korean Application No. 10-2016-7031697.
Chinese Office Action mailed Nov. 6, 2018 in corresponding/related Chinese Application No. 201710146560.1.
Korean Office Action mailed Dec. 7, 2018 in corresponding/related Chinese Application No. 10-2017-7031086.
Office Action mailed Jan. 7, 2019 in corresponding/related European Application No. 18191962.2.
Office Action mailed Mar. 26, 2019 in corresponding/related Japanese Application No. 2016-562744.
International Search Report and Written Opinion mailed Jan. 28, 2016 for Application No. PCT/US2014/046827 which claims benefit of U.S. Appl. No. 13/944,650, filed Jul. 17, 2013.
Japanese Office Action corresponding to Japanese Application No. 2016-562744 mailed Sep. 4, 2019.
Office Action mailed Oct. 24, 2019 in corresponding/related European Application No. 16763164.7.
Office Action mailed Nov. 21, 2019 in corresponding/related Australian Application No. 2016244068.
Office Action mailed Nov. 28, 2019 in corresponding/related Chinese Application No. 201680031174.1.
Office Action mailed Nov. 29, 2019 in corresponding/related Indian Application No. 2053/MUMNP/2014.
Office Action mailed Dec. 3, 2019 in corresponding/related Canadian Application No. 2945806.
Korean Office Action for corresponding/related KR Patent Application No. 10-2014-7031869 dated Mar. 16, 2016.
Office Action regarding corresponding/related Brazilian Patent Application No. 112014025681.0, dated Jan. 21, 2020.
Office Action regarding corresponding/related Japanese Patent Application No. 2017550635, dated Jan. 29, 2020.
Examination Report mailed May 26, 2020 in corresponding/related Australian Application No. 2019206060.
Office Action mailed May 7, 2020 in corresponding/related Chinese Application No. 201680057692.0.
Examination Report mailed Jun. 30, 2020 in corresponding/related Australian Application No. 2019204541.
Examination Report mailed Jul. 15, 2020 in corresponding/related Australian Application No. 2016315693.
Extended European Search Report mailed Jul. 22, 2020 in corresponding/related European Application No. 201692118.
Office Action mailed Sep. 11, 2020 in corresponding/related European Application No. 16763164.7.
Office Action mailed Sep. 28, 2020 in corresponding/related Japanese Application No. 2018-530653.
Second Office Action regarding Chinese Patent Application No. 201680057692.0, dated Jan. 21, 2021.
Office Action regarding Korean Patent Application No. 1020167003354 (with English Translation), dated Apr. 2, 2021.
Third Office Action regarding corresponding Chinese Application No. 2016800311741 (With English Translation), mailed May 6, 2021.
Office Action regarding Japanese Patent Application No. 2020037614 (with English Translation), dated May 10, 2021.
Canadian Office Action regarding Canadian Application No. 3076639, mailed Apr. 13, 2021.
Office Action regarding Japanese Patent Application No. 2018-530653, dated May 13, 2021.
Examination Report regarding Indian Patent Application No. 201837007628, dated Jul. 12, 2021.
Examination Report regarding Australian Patent Application No. 2020244386, dated May 28, 2021.
Office Action mailed Dec. 10, 2021, in corresponding/related European Application No. 16714680.2.
European Office Action regarding Patent Application No. 20169211.8, dated Mar. 9, 2022.
http://www.medtronic.com/us-en/healthcare-professionals/products/ear-nose-throat/powered-ent-instruments.html accessed Jun. 9, 2016.
International Search Report and Written Opinion mailed Feb. 12, 2018 in corresponding International Application No. PCT/US2017/049414.
International Preliminary Report on Patentability mailed Mar. 14, 2019 in corresponding International Application No. PCT/US2017/049414.
Office Action regarding Chinese Patent Application No. 201780067190.0, dated Apr. 24, 2020.
Third Office Action regarding Chinese Patent Appication No. 201780067190.0, dated Apr. 15, 2021.
Office Action (with translation) regarding Japanese Patent Application No. 2019-511873, dated Sep. 30, 2021.
U.S. Appl. No. 16/390,476, U.S. Pat. No. 11,406,396, filed Apr. 11, 2019, John W. Kulas.
U.S. Appl. No. 14/840,217, U.S. Pat. No. 10,265,082, filed Aug. 31, 2015, Vu, Michael.
U.S. Appl. No. 16/716,019, 2020-0113582, filed Dec. 16, 2019, John W. Kulas.

(56) References Cited

OTHER PUBLICATIONS

U.S. Appl. No. 17/029,437, 2021-0000488, filed Sep. 23, 2020, John W. Kulas.
Canadian Office Action regarding Patent Application No. 2997094, dated Aug. 12, 2022.

* cited by examiner

SURGICAL BURS

CROSS-REFERENCE TO RELATED APPLICATIONS

The application is a continuation of U.S. patent application Ser. No. 16/390,476 filed on Apr. 22, 2019, which is a divisional of U.S. patent application Ser. No. 14/840,217 filed on Aug. 31, 2015, now U.S. Pat. No. 10,265,082. The entire disclosure of the above applications are incorporated herein by reference.

FIELD

The disclosure relates to a surgical systems for bone cutting or shaping, and more particularly to surgical burs.

BACKGROUND

This section provides background information related to the present disclosure which is not necessarily prior art.

Surgical burs need sharp and durable cutting edges in order to efficiently dissect, cut, and/or shape bone during a surgical procedure. Human anatomy tends to locate sensitive soft tissue structures, such as nerves and blood vessels, near bones for protection. These structures can include the dura mater. Dura mater, or dura, refers to the outermost layer of protective soft tissue surrounding the brain and spinal column of a patient. During cranial and spinal procedures, the distal end of a bur can come in contact with dura mater. The term "distal" means away from a medical practitioner holding a surgical tool with a rotating bur. The term "proximal" means towards the medical practitioner and away from the patient.

It is desirable for the surgical burs to provide stability while drilling in an axial direction and to be able to efficiently cut while being moved in a radial direction. The axial direction may be, for example, a direction parallel to, along, and/or in line with a longitudinal axis of the surgical bur. The radial direction may be, for example, a direction away from and not parallel to the longitudinal axis of the surgical bur. The radial direction may be a direction away from and/or perpendicular to the longitudinal axis.

SUMMARY

This section provides a general summary of the disclosure, and is not a comprehensive disclosure of its full scope or all of its features.

A surgical bur is disclosed, the bur may include flutes and lands. Each of the flutes includes a cutting edge, rake surfaces, and a clearance surface. Each of the lands is disposed between a pair of the flutes. Each of the flutes may have multiple rake surfaces with respective rake angles. Each of the lands is disposed between a pair of the flutes.

A surgical bur may further include a trailing edge that follows the cutting edge. In operation, the surgical bur may rotate so that a cutting edge is configured to cut bone as the surgical bur rotates in a selected direction. The trailing edge may follow the cutting edge as the surgical bur rotates. The trailing edge may also engage bone, but not cut the bone.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The following description includes disclosure of rotatable surgical burs (also referred to below as the surgical burs). Cutting edges and trailing edges, as disclosed below. The surgical burs may include one or more of a plurality of external geometries, such as a ball, a cylindrical, an oval, or other generally known shape, such as the Midas Rex® surgical burs sold by Medtronic, Inc. having a place of business in Minneapolis, MN Surgical burs, including those disclosed herein, may be driven by high speed drills, such as the Midas Rex® Legend EHS Stylus High-Speed Surgical Drill which may be appropriate for a wide range of surgeries, including spine, neurology, and ear-nose-throat (ENT) procedures. The drills may drive the burs at appropriate and selectable speeds, such as about 200 to 75,000 rotations per minute (rpm), including about 7,000 to 70,000 rpms.

Example embodiments will now be described more fully with reference to the accompanying drawings. The following description is merely exemplary in nature and is not intended to limit the present disclosure, application, or uses. For example, although a human patient is illustrated as a subject, it is under stood that a subject may be any appropriate subject. Further, the subject may include inanimate and non-living subjects. Non-living subjects may include solid working materials such as a objects formed of wood, ceramics, metal, etc. Certain tissues, such as bone tissue, may be rigid and may be shaped with a cutting tool. It should be understood that throughout the drawings, corresponding reference numerals indicate like or corresponding parts and features.

Figure 1:
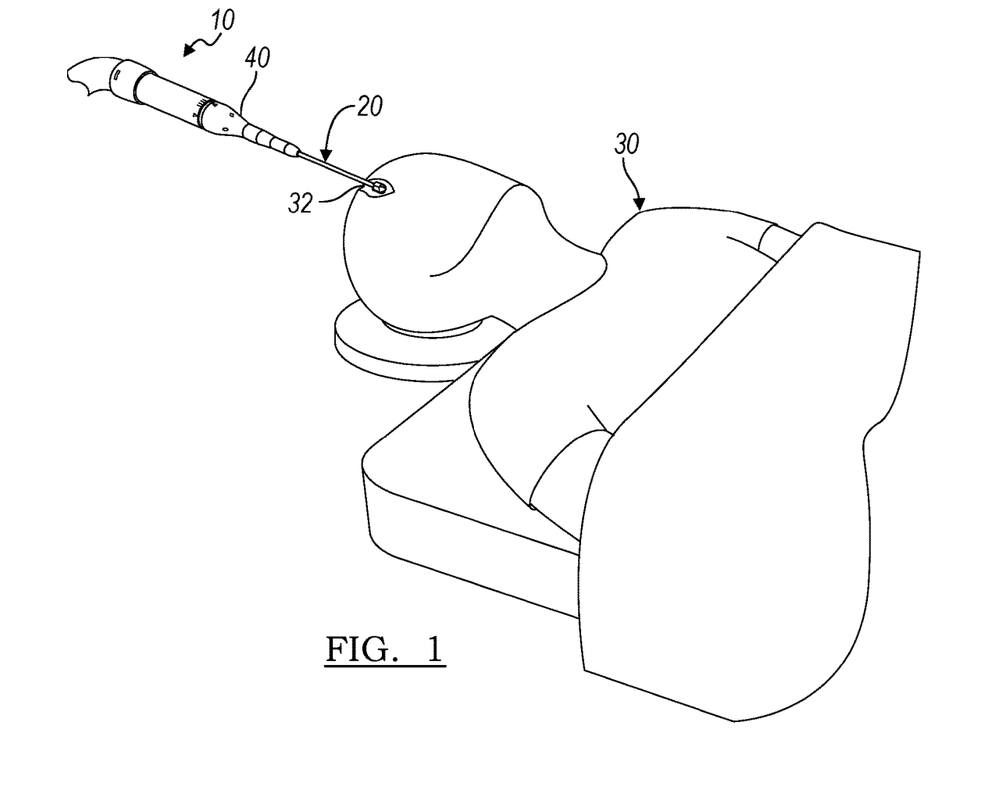
FIG. 1 is a perspective environmental view of a surgical dissection cutter assembly incorporating a surgical bur and in use on a patient in accordance with an embodiment of the present disclosure.

FIG. 1 shows a surgical dissection cutter assembly 10 incorporating a dissection tool 20 in use on a patient 30 at a surgical access site 32. The patient 30 is illustrated as undergoing a neurological operation. Access to a brain or other neurological structures of the patient 30 often requires delicate dissection of bone (e.g. a skull) and other tissues. FIG. 1 is provided for example purposes only; the surgical burs disclosed herein may be used in different tools and/or cutter assemblies and may be used for other procedures and/or operations. The dissection cutter assembly 10 includes a dissection tool driver 40, which is being utilized to dissect a portion of bone and adjacent tissue of the patient 30 in the surgical access site 32. The tool driver may include the Midas Rex® Legend EHS Stylus High-Speed Surgical Drill, as noted above, or other appropriate driver.

Figure 2:
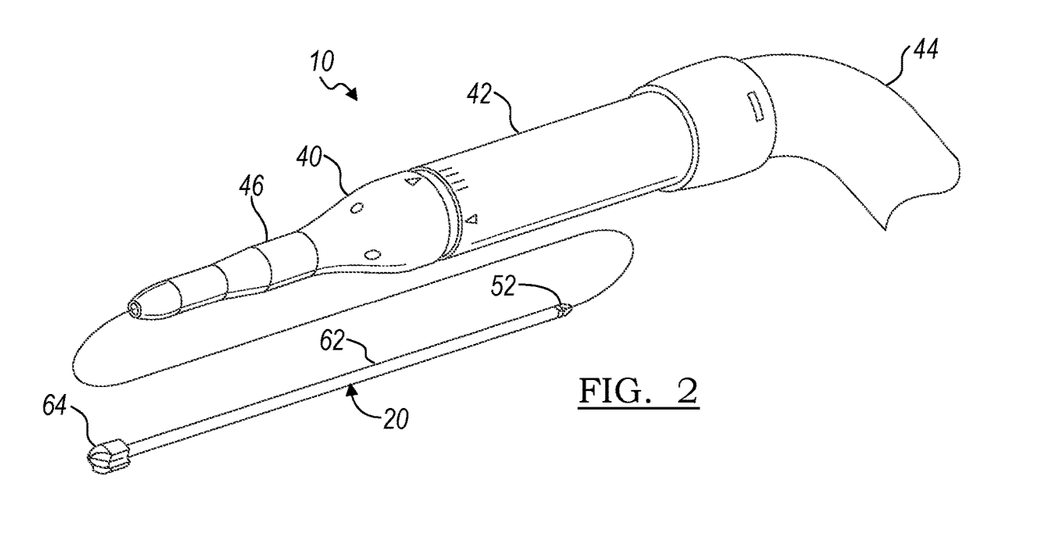
FIG. 2 is a perspective view of the surgical dissection cutter assembly of FIG. 1.

FIG. 2 is a perspective view of the surgical dissection cutter assembly 10. The dissection tool driver 40 includes a motor housing 42 connected to a connector 44, the connector may include a hose or cable assembly. The connector 44 supplies external power and control for a motor included within the motor housing 42. The dissection tool driver 40 further includes an attachment housing 46 that connects to the dissection tool 20. A dissection tool distal end includes a surgical bur 64. A dissection tool proximal end may include a driver connection 54. The driver connection 54 may engage a connection within the attachment housing 46 to receive rotary power from the motor within the motor housing 42.

Although the following described dissection tools, for example surgical burs, are disclosed and illustrated in the drawings as having a particular number of flutes, rake surfaces per flute, rake angles per flute, clearance surfaces per flute, lands, axial relief surfaces, clearance surfaces, etc., the surgical burs may have other quantities of each of these items.

Figures 3, 4:
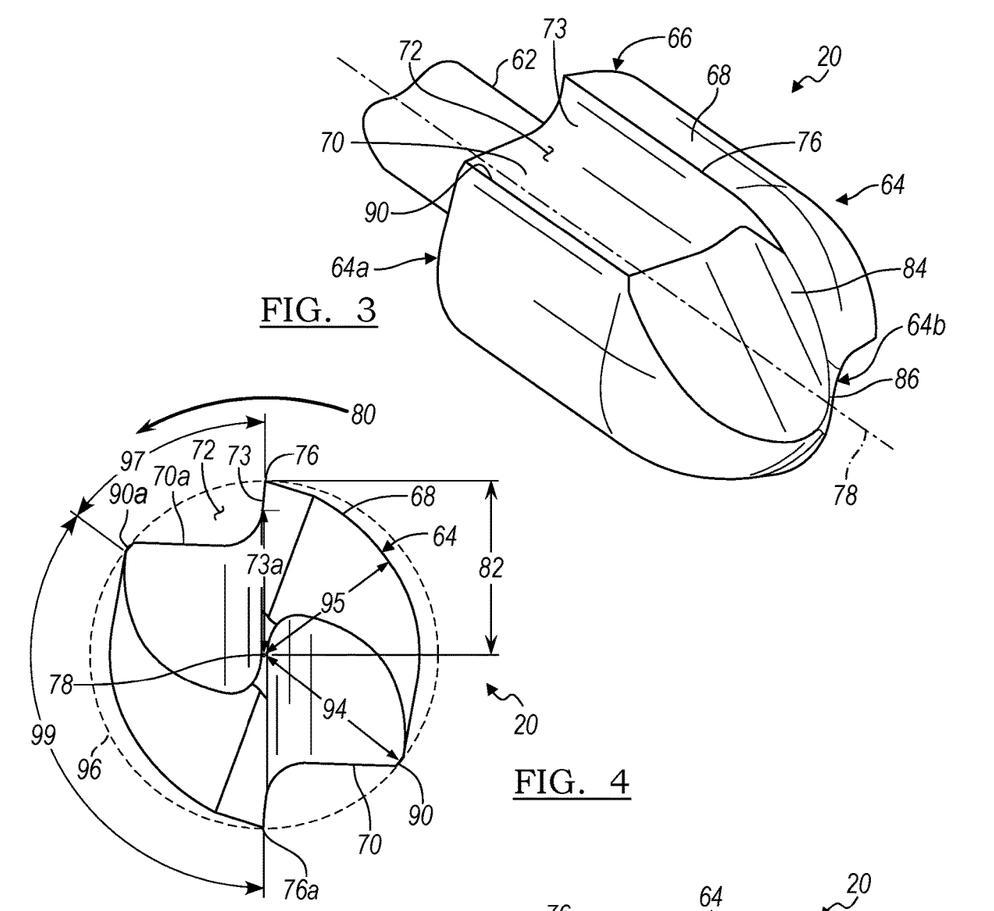
FIG. 3 is a detail front perspective view of a surgical bur.
FIG. 4 is a front detail view of the surgical bur of FIG. 3.

FIG. 3 shows a side and perspective view of the dissection tool 20. The dissection tool 20 may be used as part of the dissection assembly 10 of FIG. 1. The dissection tool 20 includes a shaft 62 and the surgical bur 64. The surgical bur 64 has a design that may generally be referred to as a "match head", "neuro", or "matchstick" design and includes a body 66. The body 66 has two convex lands 68 and two flutes 70. Each of the flutes 70 is located between the lands 68 and has a corresponding chip space 72. The lands 68 are convex-shaped and/or rounded and may be in respective 180° locations about a longitudinal axis 78 of the dissection tool 20, the shaft 62, and/or the surgical bur 64. The surgical bur 64 is rotated about the longitudinal axis 78. The flutes 70 may also be in respective 180° locations about the longitudinal axis 78. Each of the flutes 70 has one or more rake surfaces on or at a cutting edge 76. A clearance surface 73, which may be a flat or concave surface, may also correspond to the cutting edge 76. The clearance surfaces 73 are formed relative to the flutes 70, and may be on both proximal and distal portions of the flutes 70, near respective bur proximal end 64a and bur distal end 64b.

Figure 5:
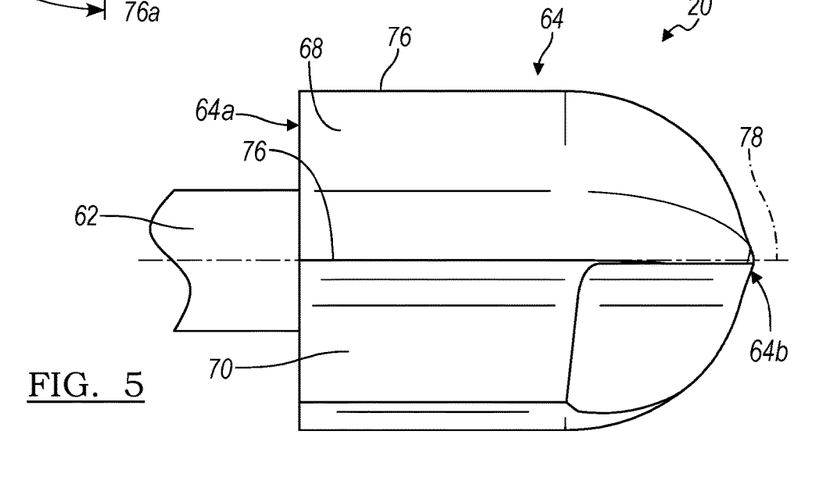
FIG. 5 is a side view of the surgical bur of FIG. 3.

With additional reference to FIGS. 4 and 5, the surgical bur 64 further includes the cutting edge 76. The cutting edge 76 is spaced a distance 82 from a center or central axis 78 of the bur 64. Generally, the cutting edge 76 axially extends from and is spaced the distance 82 from the center axis 78. Further, the cutting edge 76 is generally set on an edge of the flute 70. The cutting edge 76 is a leading edge while cutting the bur 64 rotates in the direction of arrow 80 around the central point or axis 78. The cutting edge 76 offset the distance 82 generally places the cutting edge 76 at a maximum distance from the center point 78 of the bur 64. That is the cutting edge 76 is generally at a most exterior point or distance from the center 78 as the cutting edge 76 is cutting into a material, as discussed further herein. A rig surface 84 extends from the cutting edge towards a distal tip 86 at the bur distal end 64b, through which the central axis 78 may extend. The distal tip 86 may be a terminal distal tip of the dissection tool 20.

A trailing edge 90 of the bur 64 can be formed at an edge of the curved land 68 and generally adjacent to the flute 70 of the bur 64. The trailing edge 90 is generally an edge of the curved land 68 that follows the cutting edge 76 as the bur 64 rotates in the direction of arrow 80. The trailing edge 90 may be at a distance 94 from the center axis 78. The distance 82 of the cutting edge 76 from the central axis 78 and the distance 94 of the trailing edge 90 from the central axis 78 may be substantially the same or identical. With continuing reference to FIG. 4, the leading edge 76 and the trailing edge 90 may generally lie on a circle 96 having a radius that is substantially equivalent to or defined by the distances 82 and 94 from the center 78. Thus, the cutting edge 76 may not extend beyond the circle 96 or the trailing edge 90. Both the cutting edge 76 and the trailing edge 90 may extend only to the circle 96. Moreover, the cutting edge and the trailing edge may be include more than one of each, as discussed herein. A third distance 95 of a surface forming the convex land 68 may be less than either of the first distance 82 or the second distance 94. Further, the clearance area 73 of the flutes, as discussed herein, may have a fourth distance 73a from the center 78 that is less than the first, second or third distance.

As further illustrated in FIG. 4, two flutes may be included with the surgical bur 64. A second flute 70a may include a second leading or cutting edge 76a and a second trailing edge 90a. Thus, the bur 64 may include two flutes 70, 70a with equivalent two cutting edges 76, 76a and two trailing edges 90, 90a. The second cutting edge 76a and second trailing edge 90a may also be formed on the circle 96 centered on the central axis 78 of the bur 64.

The bur 64 may include any selected geometry for forming a dissection of a selected structure. For example, the flute may define an arc 97 that is about 5 degrees (°) to about 35°. The curved land 68 may also define an arc 99, which may also be the arcuate distance from the trailing edge 90, 90a to a cutting edge 76, 76a that is about 175° to about 145°. The arcs 97, 99, however, may be formed with the bur 64 to be any selected arcuate angle. The distances 82, 94 of the cutting edges 76, 76a and the trailing edge 90, 90a, however, may all generally be equivalent.

Figures 6, 7:
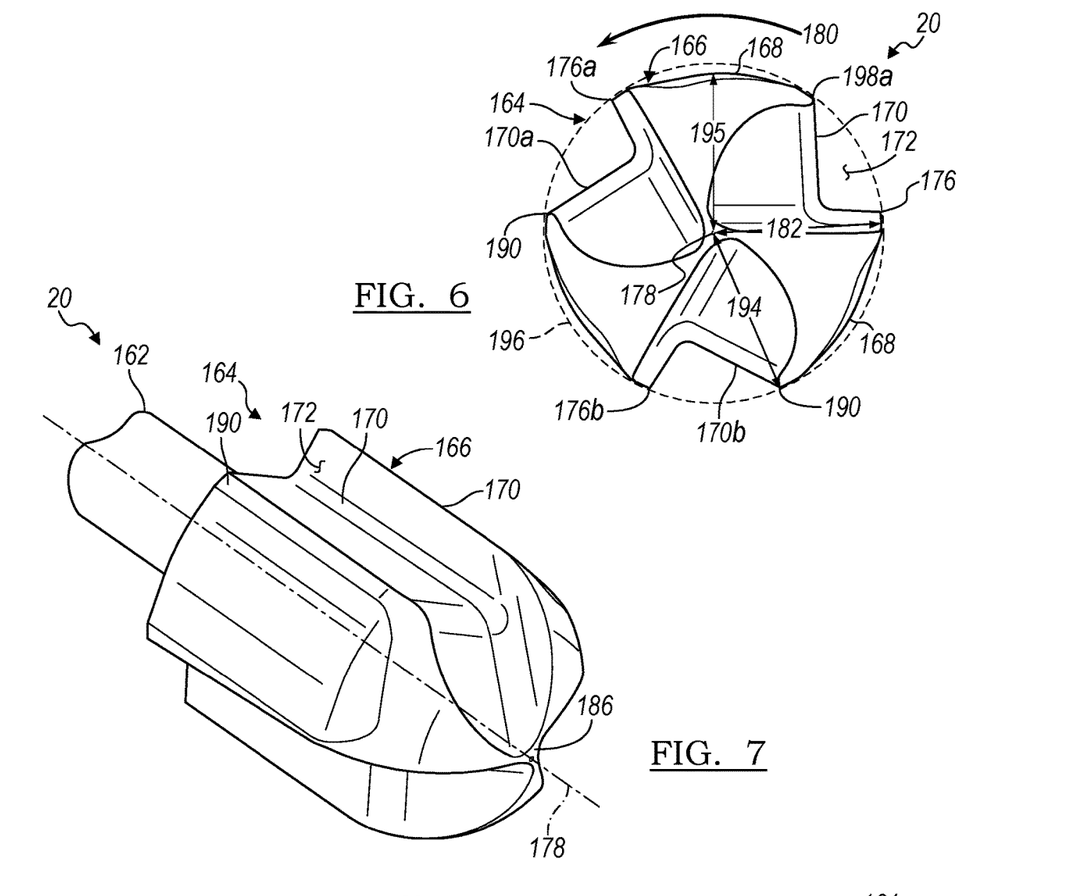
FIG. 6 is a detail front perspective view of a surgical bur.
FIG. 7 is a front detail view of the surgical bur of FIG. 6.
Figure 8:
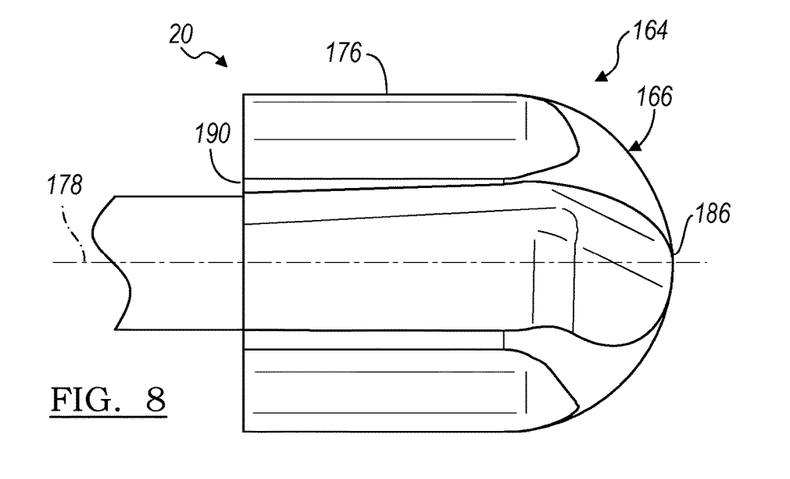
FIG. 8 is a side view of the surgical bur of FIG. 6.

Turning reference to FIGS. 6-8, a surgical bur 164 is illustrated. The surgical bur 164 can be used as the dissection tool 20 in the assembly 10 in the manner similar to the surgical bur 64, as discussed above. The surgical bur 164 can also include various features and portions similar to the surgical bur 64, as discussed above. Accordingly, this portion will not be described in substantial detail and have similar reference numerals as those noted above increased by 100.

The surgical bur 164 may include a central axis 178 that extends through a shaft 162 of the surgical bur 164. The surgical bur 164 includes a body 166. The surgical bur 164 can include a flute 170 with a cutting edge 176. Further, a trailing edge 190 can be formed on the body 166 and follow the cutting edge 176 as the surgical bur 164 rotates in a direction of arrow 180. Further, a chip collection area 172 can be defined in the flute 170. A convex land 168 is formed between the cutting edge 176 and the trailing edge 190.

The surgical bur 164 may differ from the surgical bur 64 in that the surgical bur 164 includes three cutting edges 176, 176a and 176b. Accordingly, the surgical bur 164 can also include three flutes 170, 170a and 170b. Further, the surgical bur can include three trailing edges 190, 190a and 190b.

Similar to the surgical bur 64, the surgical bur 164 can define or have a circle 196 that defines an outer perimeter or edge of the surgical bur 164. Accordingly, the cutting edge 176 may be formed at a distance 182 from the central axis 178. The trailing edge 190 can be formed at a distance 194 from the central axis 178. The distance 182 may be substantially equal or equivalent to the distance 194. Therefore, the cutting edge 176 and the trailing edge 190 can both be positioned on the circle 196. Additionally, the surgical bur may include a distal tip 186 that is generally on the axis 178 and other features that are similar to the surgical bur 164. Also, the convex land 168 may have a surface that is a third distance 195 from the center axis 178 that is less than either of the first distance 182 or the second distance 194.

The surgical bur 164, therefore, includes three flutes 170, 170a, 170b while the surgical bur 64 includes two flutes. On the bur 164, the arcuate distance of the flutes 170, 170a, 170b and the arcuate distance from a trailing edge to the next cutting edge 176, 176a, 176b may be selected to be any appropriate distance. The arcuate distances between the various portions may be smaller than on the bur 64 given that there are a greater number of flutes on the bur 164.

It is further understood that a surgical bur, according to the various embodiments, can include any appropriate number of flutes. Regardless, the cutting edge and trailing edge may both be generally on a circle that defines an outer extent of the surgical bur. Therefore, the distance from the central axis to the cutting edge and trailing edge may generally be substantially equivalent or identical, as discussed above. Further, it is understood that the surgical bur may be formed in any appropriate shape such as including a ball shape, a cylindrical shape, or other appropriate shape. The surgical bur, according to various embodiments, can therefore be used to form a dissection or resection of an appropriate portion of a subject, such as the patient 30 as illustrated in FIG. 1 and discussed further herein.

Figure 9A:
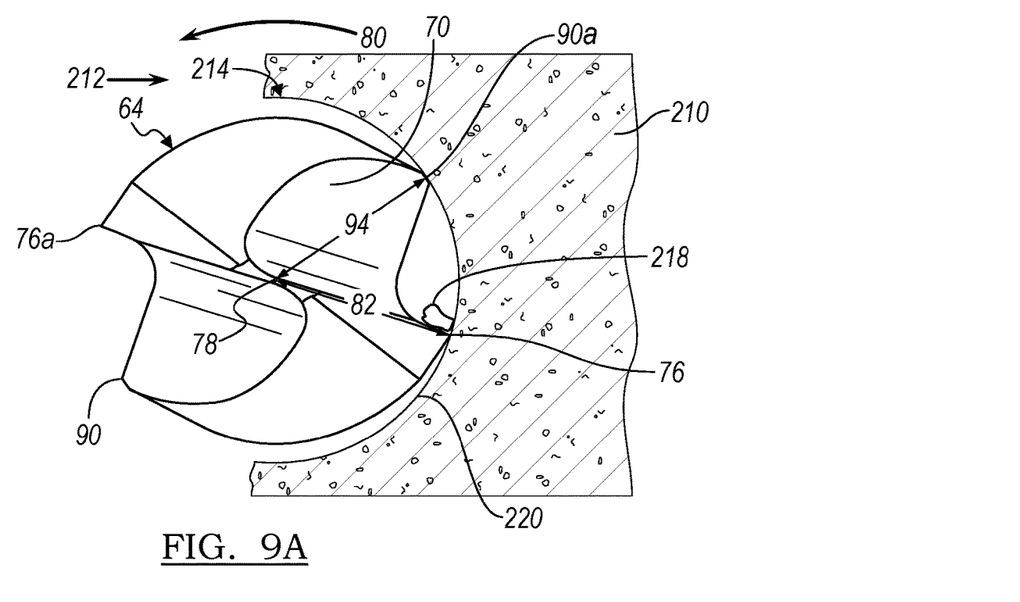
FIG. 9A is a detail environmental view of the surgical bur of FIG. 3 in use in a first position.
Figure 9B:
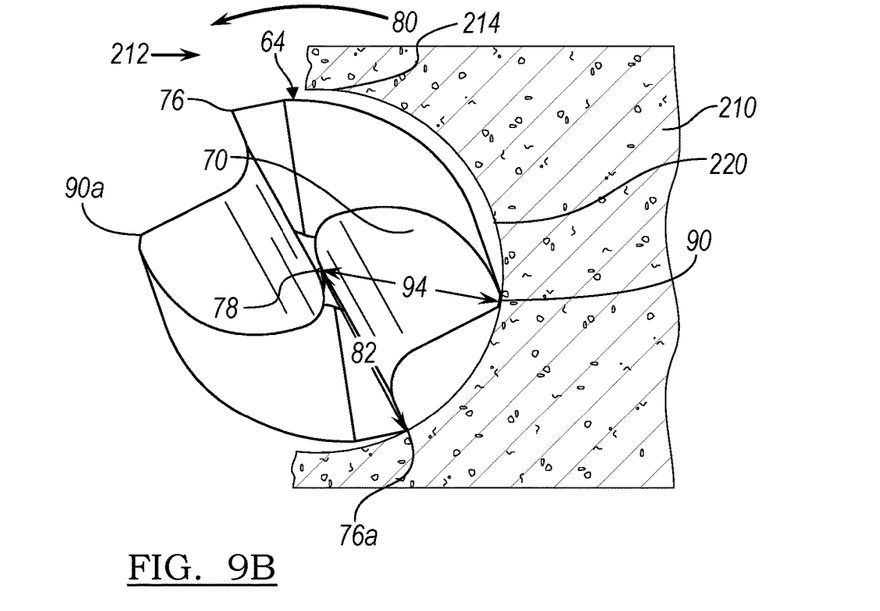
FIG. 9B is a detail environmental view of the surgical bur of FIG. 3 in use in a second position.

Turning reference to FIGS. 9A and 9B, the surgical bur 64 is illustrated relative to a bone structure or mass 210. The surgical bur 64 includes the cutting edge 76 and the cutting edge 76a, as discussed above. The surgical bur 64 can move or bore axially generally along the axis 78 of the dissection tool 20. Accordingly, as illustrated in FIGS. 9A and 9B, the surgical bur 64 can move along the axis 78 and generally directly out of the plane of the page. An additional movement of the surgical bur 64 can be to cut radially or generally away from the central axis 78, such as in the direction of arrow 212. As the surgical bur is moved in the direction of arrow 212 into the bone mass 210, a channel or trough 214 may be formed. In forming the channel 214, the cutting edge 76 can form one or more bone chips 218 from the bone mass 210. The bone chips 218 can be moved into the flute 70 of the surgical bur 64. In moving into the flute 70 of the surgical bur 64, the bone chip 218 can be moved out of the cutting path of the surgical bur 64, which generally in the direction of arrow 212.

The surgical bur 64, in cutting the bone 210, is rotating in the direction of arrow 80, as discussed above. Further, the bur 64 is moved in the direction of arrow 212 to form the channel 214 in the bone 210. Therefore, the cutting edge 76, moving in the direction of arrow 80, cuts the bone chip 218 and then continues to rotate in the direction of arrow 80 and generally away from a front wall or cutting area 220 of the channel 214. The cutting edge 76 in forming the bone chip 218, therefore, moves the bone chip 218 towards the already formed portion of the channel 214.

As illustrated in FIG. 9B, the cutting edge 76, after forming the bone chip 218, is passing into or through the formed portion of the channel 214 and the trailing edge 90 trailing as the cutting edge 76 is engaging the front or forming wall 220 of the channel 214. As discussed above, the trailing edge 90 can include the distance 94 from the central axis 78 that is substantially equivalent or equal to the distance 82 of the cutting edge 76 from the central axis 78. Therefore, the trailing edge 90 can engage the wall 220 at substantially the same distance from the central axis 78 as the cutting edge 76 and the forthcoming second cutting edge 76a. This an guide and or stabilize the bur 64, as discussed further herein, during cutting with the cutting edge 76a.

The cutting edge 76a includes a distance 82a which is substantially identical to the distance 82 from the central axis 78. Therefore, the cutting edge 76a, prior to cutting the wall 220, is generally at substantially the same position as the trailing edge 90. Because the radius or distance from the central axis 78 to the wall 220 is substantially identical for the trailing edge 90 and the second cutting edge 76a, there is no jump or jerking of the bur 64 prior to the second cutting edge 76a initiating a cut and formation of the bone chip 218. Therefore, the trailing edge 90 can form or act as a stabilizing edge or surface relative to the wall 220 of the channel 214 prior to the second cutting edge 76a cutting the wall 220. Similarly, the second trailing edge 90a can act as a stabilizing surface or edge relative to the cutting edge 76 prior to the cutting edge 76 cutting the forward wall 220 of the channel 214.

The bur 64 can rotate by the motor generally at a selected rotational rate, such as about 700 to about 75,000 rpm. As an example, the bur 64 may rotate at about 7,000 rpm. Therefore, the engaging of the cutting edges 76 and 76a on the forward wall 220 and the stabilizing by the trailing edges services 90, 90a, can substantially stabilize the bur 64 as the bur 64 forms the channel 214.

Returning reference to FIG. 9A, the bur 64 is stabilized during radial cutting, for example when the cutting edge 76 forms the bone chip 218 to cut or dissect the bone 210. The bur 64 may experience reduced vibrational and forces and chatter during radial cutting. In one example, the bur 64 can experience a reduction of vibration by at least about 40%, including a reduction of about 20-40%, including about 42%. Vibration forces may be measured with an accelerator and reported in g-forces using units such as meters/second$^2$.

During operation, the stabilization may occur by the bur 64 rotating within the channel, the cutting edge 76 moves away from the front wall 220 of the channel 214. As the cutting edge 76 moves away from the front wall 220, the trailing edge 90 can engage the wall 220 prior to the next cutting edge 76a. Due to the rotational speed of the bur 64, the elapsed time between the cutting edge leaving the wall 220 and the trailing edge 90 engaging the wall may be very short, such as on the order of micro-seconds.

The trailing edge 90, however, engages the wall 220 prior to the second cutting edge 76a beginning the cut of the front wall and formation of the bone chip 218. Therefore, as the cutting edge 76a begins to cut the front wall 220 of the channel 214, the bur 64 may be substantially stabilized relative to the front wall 220. This is at least because the trailing edge 90 is the same or substantially the same distance from the center 78 as the cutting edge 76a.

Further, the trailing edge 90 can continue to ride along the wall 220 to stabilize the bur 64 as the bur 64 rotates in the direction of arrow 80 and the cutting edge 76a cuts and forms bone chips along the wall 220. Therefore, the trailing edge may act as a guide that stabilizes the bur 64. The trailing edge 90 stabilizes the bur 64 as following cutting edge, for example the cutting edge 76a, follows the trailing edge 90 as illustrated in FIG. 9B. This assists in stability of the bur 64 during cutting the channel 214.

The contact of the trailing edge 90 with the front wall substantially simultaneously with the cutting edge 76a or immediately prior to may reduce chatter or vibration of the bur 64 while cutting or dissecting. This can reduce user fatigue during use of the assembly 10 including the bur 64. This can also increase precision of the dissection when using the bur 64 due to reduced vibration and chatter. Thus, a user may be able to cut longer without a break to decrease time needed for a procedure and to increase precision of a cut. Accordingly, the bur 64 may also decrease a chance of a mic-cut. It is further understood, as discussed above, that the trailing edge and cutting edge may be any appropriate combination of edges and need not specifically be the ones referred to by reference number above.

In cutting the channel 214, various surgical procedures may occur. For example, a bur hole may be formed in a scalp, as illustrated in FIG. 1. The bur hole may be used to allow access to the brain dura and brain tissue for various procedures, such as placement of a deep-brain simulation probe, a resection of a tumor, and the like. Further, other procedures may include forming a hole in other cranial tissues, forming a depression or removal of tissue and other bone matter, including long bones and vertebrae, and other appropriate procedures. Regardless of the specific procedure, however, the bur 64 may cut the channel 214 and the bone 210 without substantial vibration due to the positioning of the trailing edge 90 at substantially the same radial position relative to the central axis 78 as the cutting edge 76a.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Moreover, the design and structure of a surgical bur may be altered from the specific examples provide above, but include a trailing edge that has a distance from a center equal to or substantially equal to a following, such as an immediately following cutting edge. This may allow a substantially smooth and jitter or jump free dissection of tissue, including boney tissue.

The terminology used herein is for the purpose of describing particular example embodiments only and is not intended to be limiting. As used herein, the singular forms "a," "an," and "the" may be intended to include the plural forms as well, unless the context clearly indicates otherwise.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A surgical dissection assembly, comprising:
an elongated shaft extending from a proximal end towards a distal end;
a surgical bur at the distal end of the elongated shaft, the surgical bur including:
a first flute;
a first cutting edge; and
a first trailing edge,
wherein the first cutting edge is configured to cut tissue and spaced a first distance from a center axis of the surgical bur,
wherein the first trailing edge is spaced the first distance from the center axis of the surgical bur, and
wherein the surgical bur is configured to dissect tissue in a radial direction relative to the center axis,
wherein the first flute includes a convex land defined between the first cutting edge and the first trailing edge, the entire length of the convex land being disposed at a varying distance from the center axis, the varying distance being less than the first distance.

2. The surgical dissection assembly of claim 1, further comprising:
a bur distal tip configured to dissect axially along the center axis into the tissue.

3. The surgical dissection assembly of claim 2, wherein the convex land is formed by a wall extending from the first trailing edge.

4. The surgical dissection assembly of claim 3, wherein the surgical bur further includes a second flute having a second cutting edge and a second trailing edge;
wherein the convex land extends generally on an arc around the center axis between the first cutting edge and the first trailing edge.

5. The surgical dissection assembly of claim 1, wherein the first flute includes a plurality of flutes, wherein each flute of the plurality of flutes includes a cutting edge and a trailing edge.

6. The surgical dissection assembly of claim 1, wherein the first flute includes a chip clearing area.

7. The surgical dissection assembly of claim 1, wherein the first cutting edge and the first trailing edge are configured to allow stable radial cutting.

8. The surgical dissection assembly of claim 1, further comprising:
a motor connection at the proximal end of the elongated shaft.

9. The surgical dissection assembly of claim 1, further comprising:
a motor to drive the surgical bur for dissection of the tissue.

10. A surgical dissection assembly, comprising:
an elongated shaft extending from a proximal end towards a distal end;
a surgical bur at the distal end of the elongated shaft, the surgical bur including:
a first flute having a first cutting edge and a first trailing edge; and
a second flute having a second cutting edge and a second trailing edge;
wherein the first cutting edge and the second cutting edge are configured to cut a tissue and are both spaced a first distance from a center axis of the surgical bur,
wherein the first trailing edge and the second trailing edge are spaced the first a second distance from the center axis of the surgical bur, and wherein the surgical bur is configured to dissect tissue in a stable manner while moving in a radial direction relative to the center axis, and wherein the first and second flutes each include a convex land defined between the respective first cutting edge and the first trailing edge and between the second cutting edge and the second trailing edge, the entire length of each convex land being disposed at a varying distance from the center axis, the varying distance being less than the first distance or the second distance.

11. The surgical dissection assembly of claim 10, further comprising:
a motor configured to drive the surgical bur; and
a motor housing to house the motor and configured to be manipulated by a user to dissect the tissue with the surgical bur.

12. The surgical dissection assembly of claim 11, wherein the motor is configured to drive the surgical bur is a first rotational direction;
wherein the first trailing edge is configured to engage a surface of the tissue to be cut prior to the second cutting edge cutting the tissue.

13. The surgical dissection assembly of claim 12, wherein at least the first flute includes a chip clearing area defined therein.

14. The surgical dissection assembly of claim 11, wherein the proximal end of the elongated shaft includes a motor engaging section to transfer rotation force from the motor to the elongated shaft.

15. The surgical dissection assembly of claim 10, wherein the convex lands of the surgical bur further include a first convex land extending generally on a first arc around the center axis from the first cutting edge to the first trailing edge and a second convex land extending generally on a second arc around the center axis from the second cutting edge to the second trailing edge.

16. A surgical bur, comprising:
an elongated shaft extending from a proximal end towards a distal end and defining a central axis, the distal end including:
a first flute having a first cutting edge configured to cut tissue and a first trailing edge, the first cutting edge and the first trailing edge each spaced a first distance from the central axis of the surgical bur,
wherein the surgical bur is configured to dissect and cut tissue in a radial direction relative to the center axis, and wherein the first cutting edge and the first trailing edge are configured to facilitate stable radial cutting,
wherein the first flute includes a convex land defined between the first cutting edge and the first trailing edge, the entire length of the convex land being disposed at a varying distance from the center axis, the varying distance being is less the first distance.

17. The surgical bur of claim 16, further comprising:
a distal tip disposed at the distal end of the elongated shaft and configured to dissect tissue axially along the center axis.

18. The surgical bur of claim 17,
wherein the convex land is formed by a wall extending from the first trailing edge.

19. The surgical bur of claim 18, further comprising:
a second flute having a second cutting edge and a second trailing edge and wherein a second convex land extends generally on an arc around the center axis between the second cutting edge and the second trailing edge.

20. The surgical bur of claim 16, further comprising:
a plurality of flutes, each flute of the plurality of flutes including a cutting edge and a trailing edge.

* * * * *